United States Patent [19]

Masumori et al.

[11] Patent Number: 5,258,396
[45] Date of Patent: Nov. 2, 1993

[54] THIAZOLE DERIVATIVES

[75] Inventors: Hiroaki Masumori, Nishinomiya; Norihiko Tanno, Ibaraki; Ikutaro Saji, Suita; Yoshihiko Kimura, Osaka, all of Japan

[73] Assignee: Sumitomo Pharmaceuticals Company, Limited, Osaka, Japan

[21] Appl. No.: 871,800

[22] Filed: Apr. 21, 1992

[30] Foreign Application Priority Data

Apr. 24, 1991 [JP] Japan .................. 3-122078

[51] Int. Cl.$^5$ .................. A61K 31/425; C07D 277/42
[52] U.S. Cl. ...................... 514/370; 548/194
[58] Field of Search ............... 548/194, 195, 196; 514/370, 371

[56] References Cited

U.S. PATENT DOCUMENTS

| | | | |
|---|---|---|---|
| 3,933,838 | 1/1976 | Manghisi et al. | 260/306.8 R |
| 4,006,241 | 2/1977 | Strehlke et al. | 548/194 |
| 4,308,391 | 12/1981 | Howe et al. | 548/194 |
| 4,914,112 | 4/1990 | Ozato et al. | 514/326 |
| 5,000,775 | 3/1991 | Grabiak et al. | 71/88 |
| 5,114,959 | 5/1992 | Klausener et al. | 514/369 |

FOREIGN PATENT DOCUMENTS

| | | |
|---|---|---|
| 0248399 | 12/1987 | European Pat. Off. . |
| 0412404 | 2/1991 | European Pat. Off. . |
| 3905119 | 8/1990 | Fed. Rep. of Germany . |

OTHER PUBLICATIONS

*J. Chem. Soc., Perkins Trans. I,* (1983), pp. 1677–1680, Kaye et al.: "N,N-Disubstituted 2-Aminothizole-5-carboxylates: Preparation and Rotation of Functional Groups".

*Chemical Abstracts,* vol. 86, No. 13, Mar. 28, 1977, Columbus, Ohio, U.S.; abstract No. 89798N, p. 543.

*Primary Examiner*—Patricia L. Morris
*Attorney, Agent, or Firm*—Stevens, Davis, Miller & Mosher

[57] ABSTRACT

A novel thiazole derivative represented by the following general formula [1] and a pharmaceutically acceptable salt thereof:

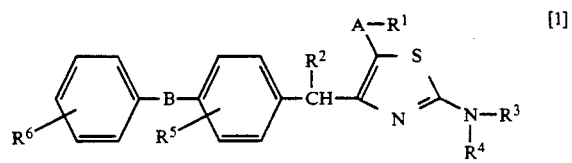

wherein A is a single bond, a straight-chained or branched lower alkylene group or a straight-chained or branched lower alkenylene group; B is a single bond or —CO—; $R^1$ is a carboxy group or —CON($R^7$)O$R^8$ ($R^7$ and $R^8$ are independently of each other a hydrogen atom or a lower alkyl group); $R^2$ is a lower alkyl group; $R^3$ and $R^4$ are independently of each other a hydrogen atom, a lower alkyl group or a lower alkoxycarbonyl group; $R^5$ is a hydrogen atom or a halogen atom; and $R^6$ is a hydrogen atom, a halogen atom, a lower alkyl group, a hydroxy group, a lower alkoxy group, a thiol group, a lower alkylthio group, a lower alkylsulfinyl group, a lower alkylsulfonyl group, a nitro group, an amino group, a substituted amino group, a cyano group, a carboxy group or an acyl group.

The compounds of the present invention are useful as therapeutic or preventive drugs for autoimmune diseases and inflammatory diseases.

8 Claims, No Drawings

THIAZOLE DERIVATIVES

BACKGROUND OF THE INVENTION

1. Field of the Invention

The present invention relates to novel thiazole derivatives useful as therapeutic and preventive agents for autoimmune diseases and inflammatory diseases.

2. Description of the Prior Art

Acidic non-steroidal anti-inflammatory drugs, gold compounds, steroids, etc. have hitherto been used as therapeutic agents for autoimmune diseases such as rheumatoid arthritis However, these drugs are limited in use because of their unreliable clinical effects and side effects. Further, as a result of the elucidations for the pathogenesis of autoimmune diseases, levamisole and D-penicillamine have become watched as etiological therapeutic agent. However, they are yet unsatisfactory because of side effects, etc.

PROBLEM TO BE SOLVED BY THE INVENTION

Ultimately, prevention and reversal of autoimmune diseases will be achieved by normalization of the immune system showing an abnormal reactivity The therapeutic agent for rheumatoid arthritis which is one of the autoimmune diseases is desired to exhibit an explicit effect not only on the chronic inflammation but also on the immunological abnormalities as a background of the inflammation. Further, since these therapeutic drugs for these diseases must be administered over a long period of time in most cases, they are required to have little side effects.

Although a variety of biologically active thiazole derivatives have hitherto been reported (for example, EP 248,399, EP 412,404), development of a therapeutic agent more excellent in the ability to control the immunological abnormality and chronic inflammation with less side effects is waited for.

SUMMARY OF THE INVENTION

With the aim of solving the above-mentioned problem, the present inventors conducted extensive studies. As the result, a compound exhibiting a strong effect in both of the immunological abnormality controlling action and chronic inflammation controlling action with less side effects was discovered. Based on this discovery, the present invention was accomplished Thus, the present invention relates to a novel thiazole derivative represented by general formula [1] or a pharmaceutically acceptable salt thereof

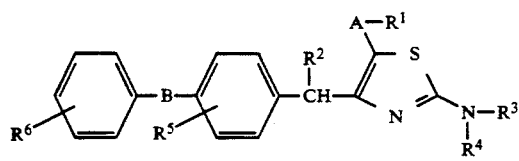

[1]

wherein A is a single bond, a straight-chained or branched lower alkylene group or a straight-chained or branched lower alkenylene group; B is a single bond or —CO—; $R^1$ is a carboxy group or —CON($R^7$)O$R^8$ (wherein $R^7$ and $R^8$ are independently of each other a hydrogen atom or a lower alkyl group), $R^2$ is a lower alkyl group; $R^3$ and $R^4$ are independently of each other a hydrogen atom, a lower alkyl group or a lower alkoxycarbonyl group; $R^5$ is a hydrogen atom or a halogen atom; and $R^6$ is a hydrogen atom, a halogen atom, a lower alkyl group, a hydroxy group, a lower alkoxy group, a thiol group, a lower alkylthio group, a lower alkylsulfinyl group, a lower alkylsulfonyl group, a nitro group, an amino group, a substituted amino group, a cyano group, a carboxy group or an acyl group.

Next, the compounds of the present invention will be explained below in more detail In the definition of general formula [1] presented above, examples of the straight-chained or branched lower alkylene group are $C_{1-4}$ alkylene groups. More suitable lower alkylene groups are methylene, ethylene, methylmethylene, trimethylene, 2-methylethylene, tetramethylene, ethylethylene and so on.

Examples of the straight-chained or branched lower alkenylene group are $C_{2-4}$ alkenylene groups. More suitable lower alkenylene examples are vinylene, 2-methylvinylene, propenylene, 2-methylpropenylene, butenylene and so on.

Examples of the lower alkoxycarbonyl group are carbonyl groups substituted by a $C_{1-4}$ alkoxy group. More suitable lower alkoxycarbonyl group are methoxycarbonyl, ethoxycarbonyl, propoxycarbonyl, 2-propoxycarbonyl, butoxycarbonyl, 2-butoxycarbonyl, 2-methylpropoxycarbonyl, 1,1-dimethylethoxycarbonyl and so on.

Examples of the lower alkyl group are $C_{1-4}$ alkyl groups. More suitable lower alkyl groups are methyl, ethyl, propyl, 2-propyl, butyl, 2-butyl, 2-methylpropyl, 1,1-dimethylethyl and so on.

The halogen atom means fluorine, chlorine, bromine and iodine

Examples of the lower alkoxy group are straight-chained or branched $C_{1-4}$ alkoxy groups. More suitable examples are methoxy, ethoxy, propoxy, 1-methylethoxy, butoxy, 1,1-dimethylethoxy and so on.

Examples of the lower alkylthio group are straight-chained or branched $C_{1-4}$ alkylthio groups. More suitable examples are methylthio, ethylthio, porpylthio, 2-methylethylthio, butylthio and so on.

Examples of the lower alkylsulfinyl group are straight-chained or branched $C_{1-4}$ alkylsulfinyl groups. More suitable examples are methylsulfinyl, ethylsulfinyl, propylsulfinyl, 2-methylethylsulfinyl, butylsulfinyl and so on.

Examples of the lower alkylsulfonyl group are straight-chained or branched $C_{1-4}$ alkylsulfonyl groups. More suitable examples are methylsulfonyl, ethylsulfonyl, propylsulfonyl, 2-methylethylsulfonyl, butylsulfonyl and so on.

Examples of the substituted amino group are monomethylamino, dimethylamino, monoethylamino, diethylamino, dipropylamino, 1-methylethylamino acid and so on.

Examples of the acyl group are acetyl, propionyl, butyryl, isobutyryl, pivaloyl and so on.

As preferably compounds of the invention, the compounds represented by general formula [2]:

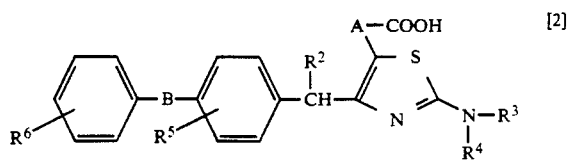

[2]

wherein A, $R^2$, $R^3$, $R^4$, $R^5$ and $R^6$ are as defined above, and pharmaceutically acceptable salts thereof can be referred to. As more preferable compounds of the invention, the compounds represented by general formula [3]:

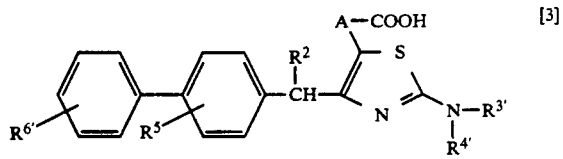

wherein $R^{3'}$ and $R^{4'}$ are each a hydrogen atom or a lower alkyl group, $R^{6'}$ is a hydrogen atom, a halogen atom or a carboxy group, and A, $R^2$ and $R^5$ are as defined above, and pharmaceutically acceptable salts thereof can be referred to. As particularly preferably compounds of the invention, the compounds represented by general formula [3']:

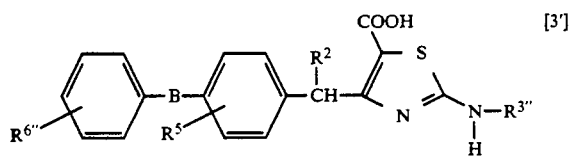

wherein $R^{3''}$ is a lower alkyl group, $R^{6''}$ is a hydrogen atom or a halogen atom and $R^2$ and $R^5$ are as defined above, and pharmaceutically acceptable salts thereof can be referred to.

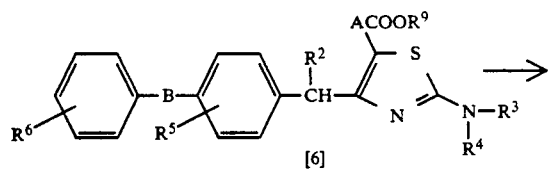

As the pharmaceutically acceptable salts of the novel thiazole derivative represented by general formula [1], salts of mineral acids such as hydrochloric acid, hydrobromic acid, sulfuric acid, phosphoric acid and the like, salts of organic carboxylic acids such as formic acid, acetic acid, fumaric acid, maleic acid, malic acid, tartaric acid, aspartic acid, glutamic acid and the like, salts of sulfonic acids such as methanesulfonic acid, benzenesulfonic acid, p-toluenesulfonic acid, hydroxybenzenesulfonic acid, dihydroxybenzenesulfonic acid and the like, salts of alkali metals such as sodium, potassium and the like, salts of alkaline earth metals such as calcium, magnesium and the like, salts of organic bases such as trimethylamine, triethylamine, pyridine and the like, ammonium salts, and the like can be referred to.

The compounds of the present invention include steric isomers, optically active isomers and tautomers, too, and all hydrates and all crystal forms, too.

The novel thiazole derivatives represented by general formula [1] can be produced, for example, according to the following methods.

Method A: The compounds of the invention represented by general formula [5]:

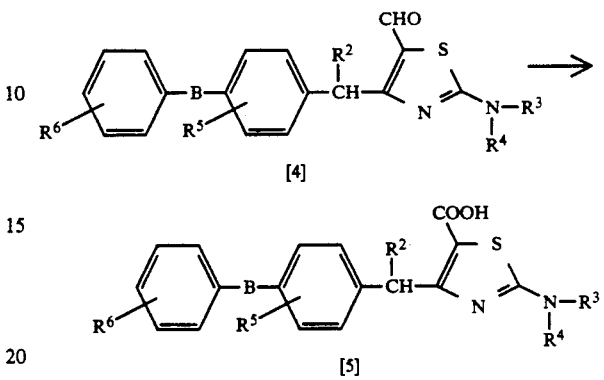

wherein B, $R^2$, $R^3$, $R^4$, $R^5$ and $R^6$ are as defined above, can be prepared by treating a compound of general formula [4] with an oxidant such as potassium permanganate, chromic acid, silver oxide, nitric acid.

As the solvent for this reaction, water is preferably used. In some cases, acids such as acetic acid, sulfuric acid can be used. The appropriate reaction temperature is selected from the range of ice-cooled temperature to the reflux temperature of the used solvent.

Method B: The compounds of the invention represented by general formula [7]:

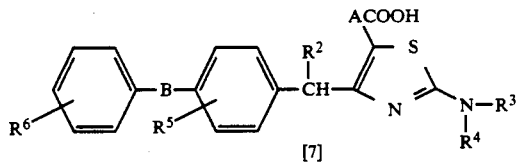

wherein $R^9$ is a lower alkyl group and A, B, $R^2$, $R^3$, $R^4$, $R^5$ and $R^6$ are as defined above, can be prepared by alkaline hydrolysis of a compound of general formula [6].

The bases which can be used in this reaction include inorganic bases such as sodium hydroxide, potassium hydroxide, sodium carbonate, potassium carbonate, organic bases such as triethylamine, imidazole and metal alkoxides such as sodium methoxide, potassium t-butoxide. The solvent preferably used in this reaction includes polar solvents such as water, methanol, ethanol and dimethyl sulfoxide If desired, the solvents can be used in the form of a mixture thereof The reaction temperature is appropriately selected from the range of room temperature to the reflux temperature of the solvent.

Method C:

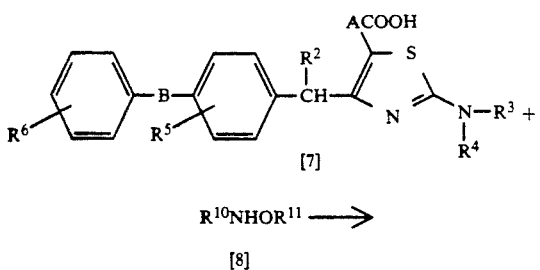

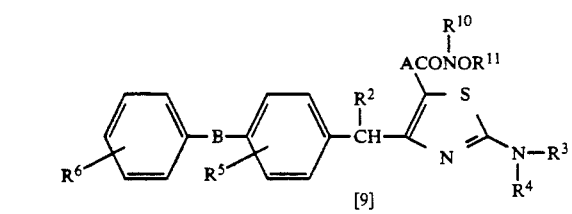

wherein $R^{10}$ and $R^{11}$ are independently of each other a hydrogen atom or a lower alkyl group and A, B, $R^2$, $R^3$, $R^4$, $R^5$ and $R^6$ are as defined above. The compound of the invention represented by formula [9] can be prepared from a compound of general formula [7] according to the method mentioned in, for example, Journal of Medicinal Chemistry, Vol. 30, Page 574 (1987). Thus, it can be prepared by treating a compound of formula [7] with oxalyl chloride in the presence of a mixture of dimethylformamide and a halogenated hydrocarbon such as methylene chloride, then dropping the reaction mixture into a solution of a compound of formula [8] in aqueous tetrahydrofuran. The reaction temperature is appropriately selected from the range of ice-cooled temperature to the reflux temperature of the solvent.

Method D:

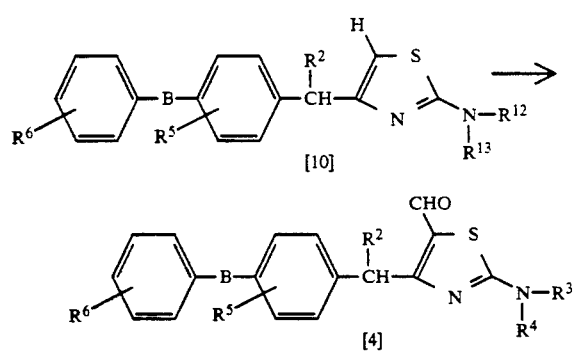

wherein $R^{12}$ and $R^{13}$ are independently of each other a lower alkyl group or a lower alkoxycarbonyl group and B, $R^2$, $R^3$, $R^4$, $R^5$ and $R^6$ are as defined above.

The compounds represented by general formula [4] can be prepared by a treatment of a compound of general formula [10] with a Vilsmeier reagent (a formylating agent using N,N-dimethylformamide or methylformamide in the presence of phosphorus oxychloride, oxalyl chloride or thionyl chloride). When one or both of $R^{12}$ and $R^{13}$ in formula [10] is (are) alkoxycarbonyl group(s), a product from which the alkoxycarbonyl group has been cleaved can be obtained under certain conditions.

As the solvent preferably usable in this reaction, halogenated hydrocarbons such as methylene chloride, chloroform, 1,2-dichlorethane can be referred to. It is also possible to use N,N-dimethylformamide as a solvent. The reaction temperature is appropriately selected from the range of room temperature to the reflux temperature of the solvent.

Method E:

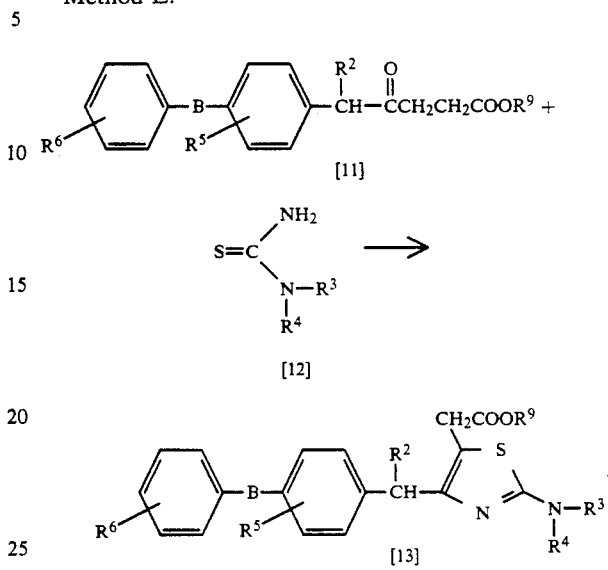

wherein $R^9$ is a lower alkyl group and B, $R^2$, $R^3$, $R^4$, $R^5$ and $R^6$ are as defined above.

The compound represented by general formula [13] can be prepared by the halogenation of the α-methylene of a compound of general formula [11] in the conventional manner (for example, by dropping bromine in an ethereal solution) followed by treatment of the product with a thiourea derivative represented by general formula [12] in an alcoholic solvent such as methanol. The preferable reaction temperature is selected from the range of room temperature to the reflux temperature of the solvent.

Method F:

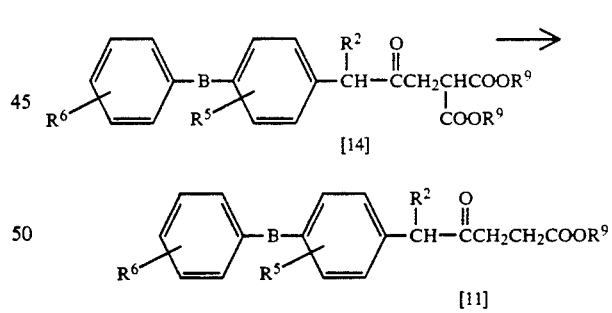

wherein $R^9$ is a lower alkyl group and B, $R^2$, $R^5$ and $R^6$ are as defined above.

The compound represented by general formula can be prepared by heating a compound represented by general formula [14] in the presence of an acid such as acetic acid and sulfuric acid.

The solvents preferably used in this reaction include dimethylformamide, dimethyl sulfoxide, ethereal solvents such as tetrahydrofuran, 1,4-dioxane and alcoholic solvents such as methanol, ethanol, butanol and isopropanol. The reaction temperature is appropriately selected from the range of 50° C. to the reflux temperature of the solvent.

Method G:

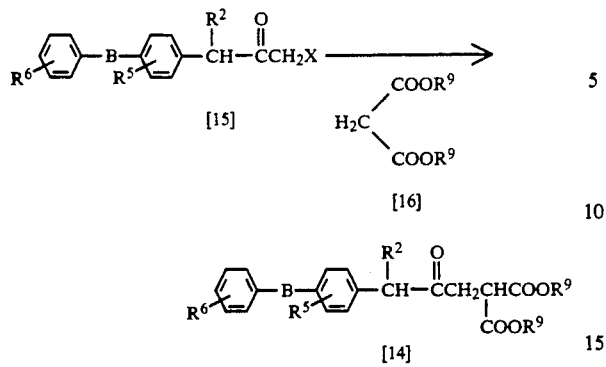

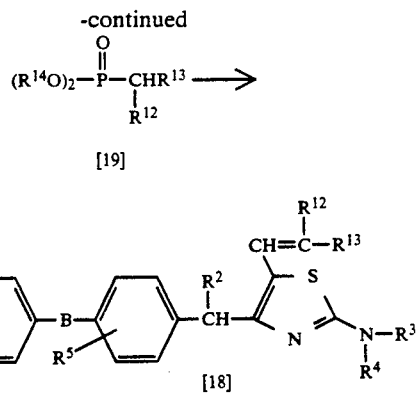

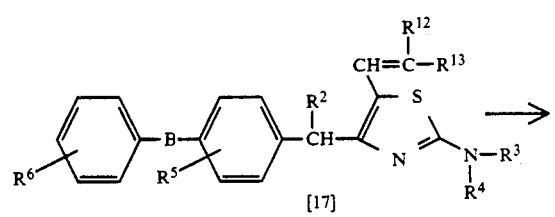

wherein $R^9$ is a lower alkyl group, X is a halogen atom and B, $R^2$, $R^5$ and $R^6$ are as defined above.

The compound represented by general formula can be prepared by a treatment of a compound represented by general formula [15] with a compound represented by general formula [16] in the presence of a base such as sodium hydride. The solvents preferably used in this reaction are dimethylformamide, dimethyl sulfoxide and ethereal solvents such as tetrahydrofuran, 1,4-dioxane. The reaction temperature is appropriately selected from the range of room temperature to the reflux temperature of the solvent.

Method H:

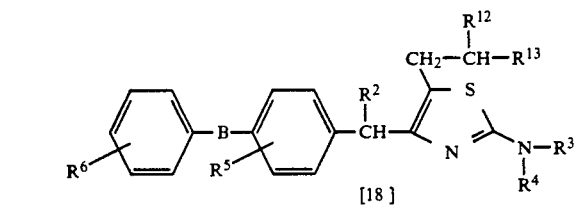

wherein $R^{12}$ is a hydrogen atom or a lower alkyl group, $R^{13}$ is a lower alkoxycarbonyl group and B, $R^2$, $R^3$, $R^4$, $R^5$ and $R^6$ are as defined above.

The compound represented by general formula [18] can be prepared by a hydrogenation of a compound of general formula [17] at ordinary temperature at ordinary pressure in an alcoholic solvent such as methanol, ethanol, 2-propanol with a catalyst such as palladium carbon (Pd/C).

Method I:

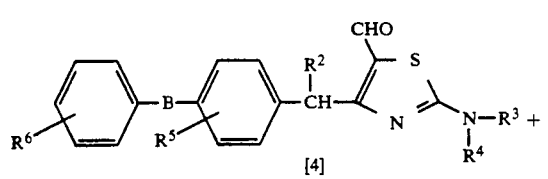

wherein $R^{12}$ is a hydrogen atom or a lower alkyl group, $R^{13}$ is a lower alkoxycarbonyl group, $R^{14}$ is a lower alkyl group and B, $R^2$, $R^3$, $R^4$, $R^5$ and $R^6$ are as defined above.

The compound represented by general formula [18] can be prepared by a treatment of a compound of general formula [4] with a compound of general formula [19] in the presence of a base such as sodium hydride, sodium methoxide.

The solvents preferably used in this reaction are amide type solvents such as N,N-dimethylformamide, dimethylacetamide, dimethyl sulfoxide, and ethereal solvents such as tetrahydrofuran, 1,4-dioxane. The reaction temperature is appropriately selected from the range of room temperature to the reflux temperature of the solvent. When B is —CO—, the reaction may be carried out after a protection of B with an acetal or the like (the reaction conditions of the acetal formation and acetal cleavage are mentioned in T. W. Greene, "Protective Groups in Organic Synthesis", John Wiley & Sons, Inc. (1981), Chapter 4, pp. 116–141.)

Method J:

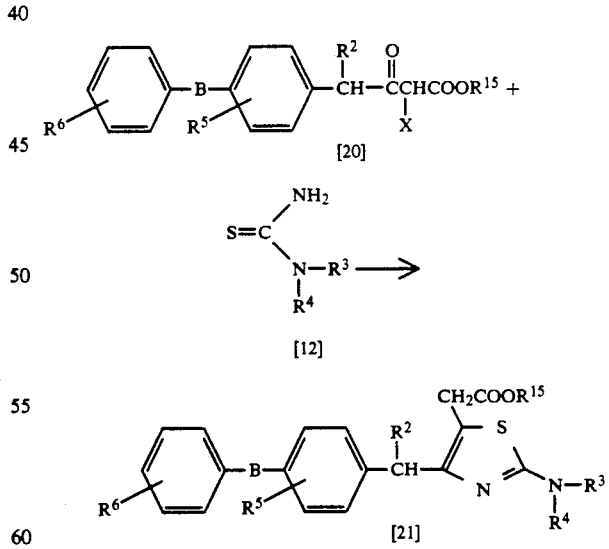

wherein $R^{15}$ is a lower alkyl group, X is a halogen atom and B, $R^2$, $R^3$, $R^4$, $R^5$ and $R^6$ are as defined above.

The compound represented by general formula [21] can be prepared by a treatment of a compound of general formula [20] with a compound of general formula [12] in an alcoholic solvent such as methanol, ethanol at an appropriate temperature selected from the range of room temperature to the reflux temperature of the solvent.

Method K:

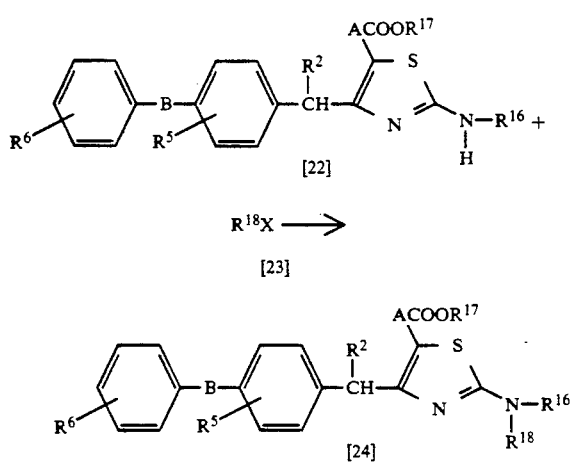

wherein $R^{16}$, $R^{17}$ and $R^{18}$ each represent a lower alkyl group, X is a halogen atom and B, $R^2$, $R^5$ and $R^6$ are as defined above.

The compound represented by general formula [24] can be prepared by a treatment of a compound of general formula [22] with a compound of general formula [23] in a mixture of an inert solvent such as benzene, toluene and 50% aqueous solution of sodium hydroxide in the presence of a phase transfer catalyst such as tetra-n-butylammonium hydrogen sulfate.

In the production methods mentioned above, the starting compounds represented by general formula [8], [10], [12], [15], [16], [19], [20] and [23] are compounds which are known in themselves or synthesizable according to known methods For example, the compounds represented by general formulas [10] and [15] can be prepared by the method mentioned in Japanese Patent Unexamined publication No. 63-152368 The compound of general formula [19] can be prepared, for example, according to the method mentioned in Chemische Berichte, Vol 92, Page 2499 (1959) or J. Am. Chem Soc, Vol. 83, Page 1733 (1961) The compound of general formula [20] can be prepared by the method mentioned in J Org. Chem , Vol. 43, Page 2087 (1978) and ibid, Vol 42, Page 1389 (1977).

In putting the compounds of the invention represented by general formula [1] and pharmaceutically acceptable salts thereof to use as a medical drug, they can be administered either orally or non-orally. That is, they can be orally administered in the conventional forms of administration such as tablet, capsule, syrup, suspension and the like. Otherwise, they can be administered non-orally by injecting their liquid preparation having a form of, for example, solution, emulsion, suspension or the like. Further, they can be administered into the rectum in the form of a suppository.

The above-mentioned desirable forms of preparation can be produced by compounding an active compound with pharmaceutically acceptable conventional carrier, diluent, binder, stabilizer, etc. When the active compound is to be used in the form of injection, pharmaceutically acceptable buffering agent, solubilizer, isotonizing agent and the like can also be added.

Although the dose and number of administration vary depending on the symptoms, age and body weight of patient and the form of administration, the dose is usually about 1–2,000 mg/day and preferably 5–1,000 mg/day per one adult in the case of oral administration. In the case of injection, its 0.05–200 mg/day is administered either in one portion or in several portions per one adult.

The compounds of the present invention and pharmaceutically acceptable salts thereof are useful as therapeutic and preventive drugs for autoimmune diseases such as rheumatoid arthritis, systemic lupus erythemato'sus, systemic scleroderma, Sjögren's syndrome disease, Hashimoto's disease, grave myoasthenia, Basedow's disease, Addison's disease, juvenile diabetes, autoimmune hemopathy (for example, aplastic anemia, hemolytic anemia, idiopathic thrombopenia, etc.), ulcerative colitis, chronic active hepatitis, glomerular nephritis, interstitial pulmonary fibrosis, etc., as well as for inflammatory diseases such as osteoarthritis, gout, atopic dermatitis, psoriasis, etc.

Thus, the compounds of the present invention exhibit marked effects in test systems involving animal models having chronic inflammations such as rat adjuvant arthritis etc. and animal models having immunological abnormalities such as mouse III allergic reaction etc. Accordingly, the compounds of the present invention are characterized not only by their explicit effect on chronic inflammations but also by affecting the immunological abnormalities which constitute a background of the inflammations. Such actions of the compounds of the invention suggest an effectiveness of the compounds of the invention on autoimmune diseases and inflammatory diseases.

Further, the compounds of the present invention are improved in intracarporal kinetics and lessened in side effects by introducing a polar group-containing functional group into the thiazole ring, so that they are considered capable of being administered over a long period of time.

WORKING EXAMPLES

Next, the present invention is illustrated by referring to the following examples and reference examples. Needless to say, the invention is by no means limited by these examples.

EXAMPLE 1

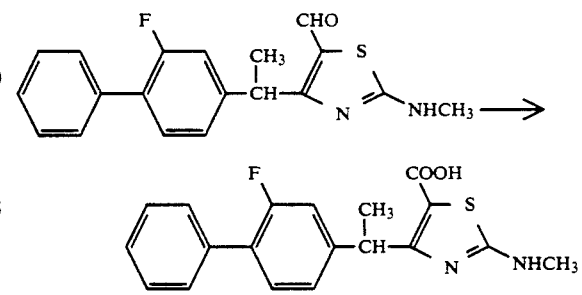

5-Formyl-4-(1-(2-fluoro-4-biphenylyl)ethyl)-2-methylaminothiazole (1.00 g, 2.9 mmoles) was dissolved in acetone (20 ml). Jones reagent (chromic acid (VI) dissolved in a mixture of concentrated sulfuric acid and water) (2 ml) was added dropwise thereinto while cooling the system with ice, after which it was stirred for one hour. Then, an additional 2 ml of Jones reagent was added dropwise and the resulting mixture was stirred for one hour. A small quantity of 2-propyl alcohol was added to the reaction mixture, it was extracted with ether, and the ether layer was washed with water and dried over sodium sulfate. The solvent was distilled off under reduced pressure, and the residue was recrystallized from ethyl acetate to obtain the desired 4-(1-(2-fluoro-4-biphenylyl)ethyl)-2-methylamino-5-thiazolecarboxylic acid (205 mg, 0.58 mmole, yield 20%) as a white crystalline product.

m.p. 133°–134° C.

EXAMPLE 2

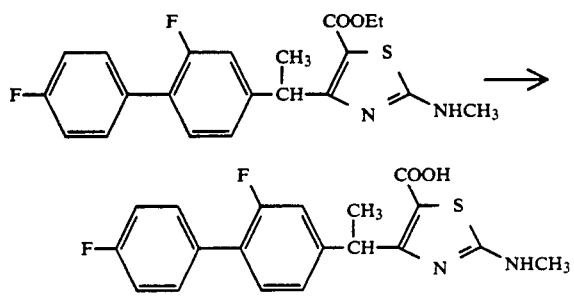

Ethyl 4-(1-(2,4'-difluoro-4-biphenylyl)ethyl)-2-methylamino-5-thiazolecarboxylate (1.00 g, 2.48 mmole) was dissolved in methanol (20 ml). After adding a solution of potassium hydroxide (420 mg, 7.49 mmole) in water (4 ml), the mixture was heated under reflux for 5 hours. The reaction mixture was concentrated under reduced pressure, and the residue was diluted with water and washed with ether. The water layer was acidified to about pH 4 with 1chloric acid and extracted with ethyl acetate. The organic layer was washed with water, dried and concentrated under reduced pressure Recrystallization of the residue from methanol gave the desired 4-(1-(2,4'-difluoro-4-biphenylyl-)ethyl)-2-methylamino-5-thiazolecarboxylic acid (599 mg, 1.60 mmoles, yield 65%) as a white crystalline product.

m.p. 195°–195.5° C.

EXAMPLE 3

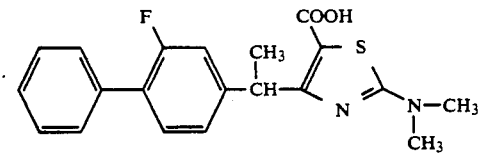

4-(1-(2-Fluoro-4-biphenylyl-)ethyl)-2-dimethylamino-5-thiazolecarboxylic acid was obtained from ethyl 4-(1-(2-fluoro-4-biphenylyl)ethyl)-2-dimethylamino-5-thiazolecarboxylate in the same manner as in Example 2.

m.p. 166.5°–167° C.

EXAMPLE 4

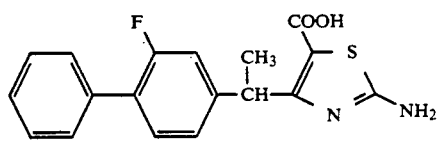

4-(1-(2-Fluoro-4-biphenylyl)ethyl)-2-amino-5-thiazolecarboxylic acid was obtained from ethyl 4-(1-(2-fluoro-4-biphenylyl)ethyl)-2-amino-5-thiazolecarboxylate in the same manner as in Example 2.

m.p. 155°–158° C.

EXAMPLE 5

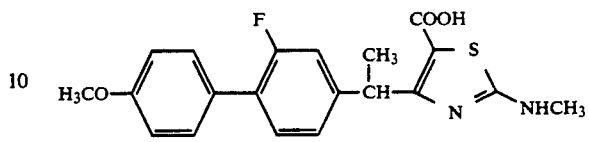

4-(1-(2-(Fluoro-4,-methoxy-4-biphenylyl)-ethyl)-2-methylamino-5-thiazolecarboxylic acid was obtained from ethyl 4-(1-(2-fluoro-4,-methoxy-4-biphenylyl)ethyl)-2-methylamino-5-thiazolecarboxylate in the same manner as in Example 2.

m.p. 167.5°–168° C. (decomposition)

EXAMPLE 6

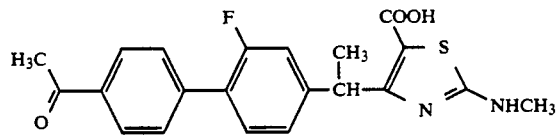

4-(1-(4'-Acetyl-2-fluoro-4-biphenylyl)ethyl)-2-methylamino-5-thiazolecarboxylic acid was obtained from ethyl 4-(1-(4'-acetyl-2-fluoro-4-biphenylyl)ethyl)-2-methylamino-5-thiazolecarboxylate in the same manner as in Example 2.

m.p. 158°–159° C. (decomposition)

EXAMPLE 7

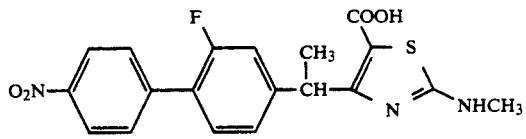

4-(1-(2-Fluoro-4'-nitro-4-biphenylyl)ethyl)-2-methylamino-5-thiazolecarboxylic acid was obtained from ethyl 4-(1-(2-fluoro-4'-nitro-4-biphenylyl)ethyl)-2-methylamino-5-thiazolecarboxylate in the same manner as in Example 2.

m.p. 158°–160° C.

EXAMPLE 8

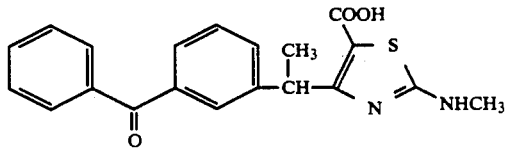

4-(1-(3-Benzoylphenyl)ethyl)-2-methylamino-5-thiazolecarboxylic acid was obtained from ethyl 4-(1-(3-benzoylphenyl)ethyl)-2-methylamino-5-thiazolecarboxylate in the same manner as in Example 2.

m.p. 154°–157° C. (decomposition)

EXAMPLE 9

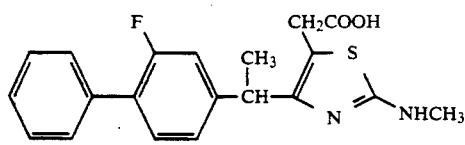

2-(4-(1-(2-Fluoro-4-biphenylyl)ethyl)-2-methylamino-5-thiazolyl)acetic acid was obtained from ethyl 2-(4-(1-(2-fluoro-4-biphenylyl)ethyl-2-methylamino-5-thiazolyl-)acetate in the same manner as in Example 2.

m.p. 102°–105° C.

EXAMPLE 10

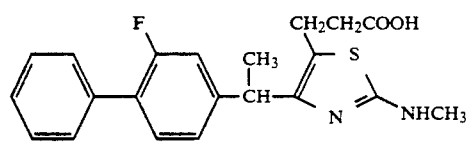

3-(4-(1-(2-Fluoro-4-biphenylyl)ethyl)-2-methylamino-5-thiazolyl)propionic acid was obtained from methyl 3-(4-(1-(2-fluoro-4-biphenylyl)ethyl)-2-methylamino-5-thiazolyl-)propionate in the same manner as in Example 2.

m.p. 179°–180° C.

EXAMPLE 11

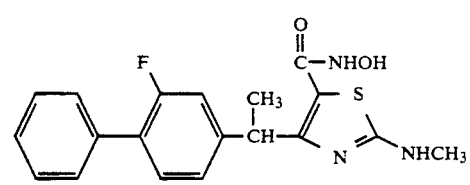

To an ice-cooled and stirred solution of 4-(1-(2-fluoro-4-biphenylyl)ethyl)-2-methylamino-5-thiazolecarboxylic acid (5.00 g, 14.0 mmoles) and dimethylformamide (1.03 g, 14.1 mmoles) in methylene chloride (200 ml) was added dropwise oxalyl chloride (3.93 g, 31.0 mmoles) and the mixture was stirred for 40 minutes. On the other hand, hydroxylamine hydrochloride (3.91 g, 56.3 mmoles) in water (5 ml) and triethylamine (8.55 g, 84.5 mmoles) were dissolved in tetrahydrofuran (100 ml), and to the mixture was added dropwise the above-mentioned reacted solution of thiazolecarboxylic acid. After stirring for 30 minutes, the reaction mixture was acidified to pH 4 with 1M hydrochloric acid and extracted with methylene chloride. The organic layer was washed with water, dried and concentrated under reduced pressure, and the residue was purified by silica gel column chromatography to obtain the desired 4-(1-(2-fluoro-4-biphenylyl)ethyl)-2-methylamino-5-thiazolecarbohydroxamic acid (2.50 g, 6.73 mmoles, 48%) as a light brown amorphous product.

m.p. 118° C.

EXAMPLE 12

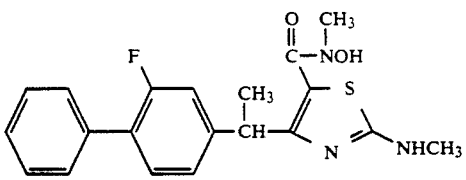

N-methyl-4-(1-(2-fluoro-4-biphenylyl)ethyl)-2-methylamino-5-thiazolecarbohydroxamic acid was obtained from 4-(1-(2-fluoro-4-biphenylyl)ethyl)-2-methylamino-5-thiazolecarboxylic acid in the same manner as in Example 12.

EXAMPLE 13

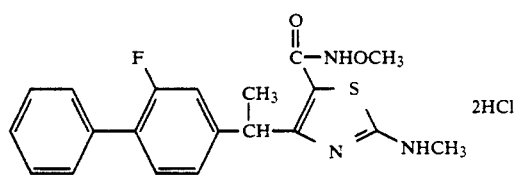

N-methoxy-4-(1-(2-fluoro-4-biphenylyl)ethyl)-2-methylamino-5-thiazolylamide dihydrochloride was obtained from 4-(1-(2-fluoro-4-biphenylyl)ethyl-2-methylamino-5-thiazolecarboxylic acid in the same manner as in Example 11.

m.p. 66°–68° C.

EXAMPLE 14

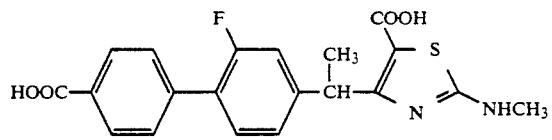

4-(1-(4'-Carboxy-2-fluoro-4-biphenylyl)ethyl)-2-methylamino-5-thiazolecarboxylic acid was obtained from ethyl 4-(1-(4'-ethoxylcarbonyl-2-fluoro-4-biphenylyl)ethyl)-2-methylamino-5-thiazolecarboxylate in the same manner as in Example 2.

m.p. 172°–175° C. (decomposition)

REFERENCE EXAMPLE 1

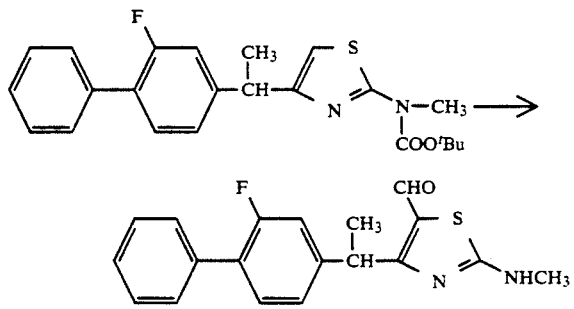

To an ice-cooled mixture of dimethylformamide (33.3 g) and 1,2-dichloroethane (110 ml) was added dropwise a solution of phosphorous oxychloride (10.5 g, 68.5 mmoles) in 1,2-dichloroethane (40 ml) and the resulting mixture was stirred at ambient temperature for 15 min.

After being cooled with ice-water bath, to the mixture was added dropwise a solution of 2-(N-t-butoxycarbonyl, N-methyl)amino-4-(1-(2-fluoro-4-biphenyl)ethyl)-thiazole (18.9 g, 45.8 mmoles) in 1,2-dichloroethane (300 ml) and the mixture was stirred at ambient temperature for 1 hr and then heated at reflux for 4 hr. The reaction solution was concentrated under reduced pressure and the afforded residue was diluted with 10% aqueous solution of sodium hydroxide (36 ml) and extracted with chloroform. The organic layer was washed with water, dried over anhydrous sodium sulfate, and concentrated under reduced pressure. The resulting residue was purified by silica gel column chromatography to give the desired 5-formyl-4-(1-(2-fluoro-4-biphenylyl)ethyl)-2-methylaminothiazole (6.9 g, 20.5 mmol, yield 45%) as a light yellow crystalline product.
m.p. 126°–128° C.

REFERENCE EXAMPLE 2

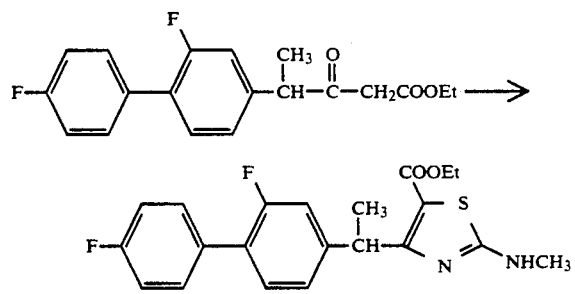

To an ice-cooled solution of ethyl 4-(2,4-difluoro-4-biphenylyl)-3-oxopentanoate (1.00 g, 3.01 mmoles) and methanol (97 mg, 3.03 mmoles) in methylene chloride (3.0 ml) was added dropwise a solution of sulfuryl chloride (427 mg, 3.16 mmoles) in methylene chloride (1 ml) and resulting mixture was stirred at the same temperature for 1 hr. The reaction mixture was concentrated under reduced pressure at 30° C. The mixture of the residue, N-methylthiourea (326 mg, 3.62 mmoles), and methanol (10 ml) was stirred at 50° C. for 1 hr. An additional 100 mg of N-methylthiourea was added to the reaction mixture and it was stirred at the same temperature for 1 hr. The residue was diluted with ethyl acetate, washed with sodium bicarbonate solution, washed with water, dried over sodium sulfate and concentrated under reduced pressure. Purification of the residue by means of silica gel column gave the desired ethyl 4-(1-(2,4'-fluoro-4-biphenylyl)ethyl)-2-methylamino-5-thiazolecarboxylate (1.06 g, 2.62 mmoles, yield 87%) as a white amorphous product.

1H-NMR (CDCl3) δ ppm : 1.35 (3H, t), 1.61 (3H, d), 2.97 (3H, d), 4.23–4.33 (2H, m), 5.21 (1H, q), 5.52 (1H, br), 7.07–7.50 (7H, m).

REFERENCE EXAMPLE 3

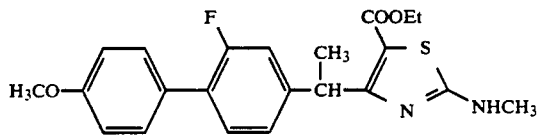

Ethyl 4-(1-(2-fluoro-4'-methoxy-4-biphenylyl)ethyl)-2-methylamino-5-thiazolecarboxylate was obtained from ethyl 4-(2-fluoro-4'-methoxy-4-biphenylyl)-3-oxopentanoate in the same manner as in Reference Example 2.

1H-NMR (CDCl3) δ ppm : 1.35 (3H, t), 1.62 (3H, d), 2.95 (3H, d), 3.84 (3H, s), 4.23–4.33 (2H, m), 5.20 (1H, q), 5.62 (1H, br), 6.93–7.47 (7H, m).

REFERENCE EXAMPLE 4

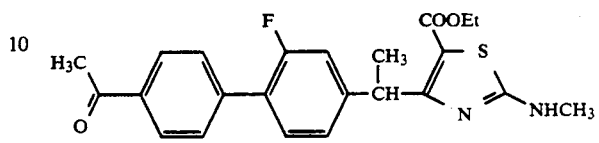

Ethyl 4-(1-(4'-acetyl-2-fluoro-4-biphenylyl)-ethyl)-2-methylamino-5-thiazolecarboxylate was obtained from ethyl 4-(4'-acetyl-2-fluoro-4-biphenylyl)-3-oxopentanoate in the same manner as in Reference Example 2.

1H-NMR (CDCl3) δ ppm : 1.34 (3H, t), 1.63 (3H, d), 2.62 (3H, s), 2.90 (3H, d), 4.28 (2H, m), 5.25 (1H, q), 6.27 (1H, br), 7.24–7.38 (7H, m).

REFERENCE EXAMPLE 5

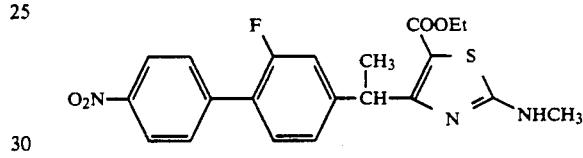

Ethyl 4-(1-(2-fluoro-4'-nitro-4-biphenylyl-)-ethyl)-2-methylamino-5-thiazolecarboxylate was obtained from ethyl 4-(2-fluoro-4'-nitro-4-biphenylyl-)-3-oxopentanoate in the same manner as in Reference Example 2.

1H-NMR (CDCl3) δ ppm : 1.34 (3H, t), 1.63 (3H, d), 2.91 (3H, d), 4.29 (2H, m), 5.26 (1H, q), 6.32 (1H, m), 7.31–7.34 (3H, m), 7.65 (2H, dd), 8.24 (2H, d).

REFERENCE EXAMPLE 6

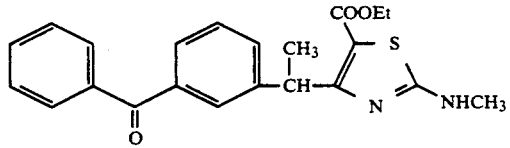

Ethyl 4-(1-(3-benzoylphenyl)ethyl)-2-methylamino-5-thiazolecarboxylate was obtained from ethyl 4-(3-benzoylphenyl)-3-oxopentanoate in the same manner as in Reference Example 2.
m.p. 176°–177° C.

REFERENCE EXAMPLE 7

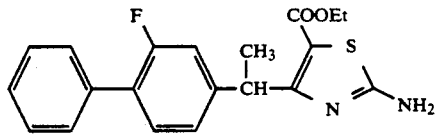

Ethyl 4-(1-(2-fluoro-4-biphenylyl)ethyl)-2-amino-5-thiazolecarboxylate was obtained from ethyl 4-(2-fluoro-4-biphenylyl)-3-oxopentanoate in the same manner as in Reference Example 2 except that the N-methylthiourea was replaced with thiourea.
m.p. 147°–148° C.

REFERENCE EXAMPLE 8

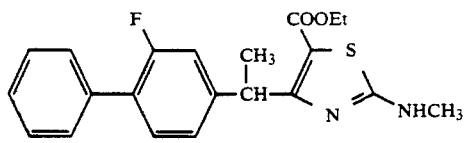

Ethyl 4-(1-(2-fluoro-4-biphenylyl)ethyl)-2-methylamino-5-thiazolecarboxylate was obtained from ethyl 4-(2-fluoro-4-biphenylyl)-3-oxopentanoate in the same manner as in Reference Example 2.

m.p. 108°-109° C.

REFERENCE EXAMPLE 9

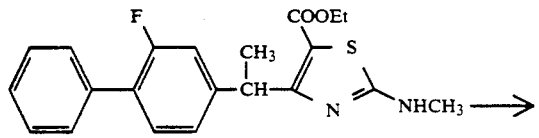

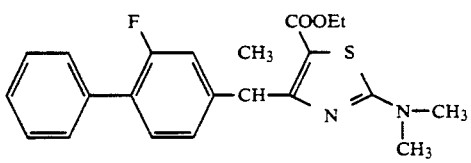

To a solution of ethyl 4-(1-(2-fluoro-4-biphenylyl)-ethyl)-2-methylamino-5-thiazolecarboxylate (3.55 g, 9.23 mmoles) and methyl iodide (2.81 g, 18.8 mmoles) in benzene (70 ml) were added 50% aqueous solution of sodium hydroxide (35 ml) and tetra-n-butylammonium hydrogen sulfate (3.13 g, 9.22 mmoles) and the resulting mixture was stirred at room temperature for 5.5 hours. The reaction mixture was diluted with water, acidified to pH 6 with 1M hydrochloric acid and extracted with ethyl acetate. The organic layer was washed with water, dried over sodium sulfate and concentrated under reduced pressure. Purification of the residue by means of silica gel column gave the desired ethyl 4-(1-(2-fluoro-4-biphenylyl)ethyl)-2-dimethylamino-5-thiazolecarboxylate (3.68 g, 9.23 mmoles, quantitative yield) as a colorless oil.

1H-NMR (CDC13) δ ppm : 1.34 (3H, t), 1.64 (3H, d), 3.14 (6H, s), 4.27 (2H, m), 5.18 (1H, q).

REFERENCE EXAMPLE 10

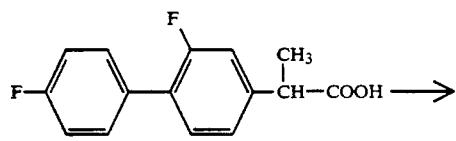

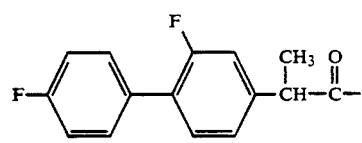

To a suspension of 2-(2,4,-difluoro-4-biphenylyl)propionic acid (1.20 g, 4.58 mmoles) in toluene (10 ml) were added dimethylformamide (2 drops) and thionyl chloride (1.09 g, 9.16 mmoles) and the resulting mixture was stirred at 80° C. for 2 hours. The reaction mixture was concentrated with toluene under reduced pressure to remove the excess thionyl chloride. To a solution of Meldrum's acid (1.32 g, 9.16 mmoles) and pyridine (1.45 g, 18.3 mmoles) in 1,2-dichloroethane (15 ml) was added dropwise a solution of the acid chloride obtained above in 1,2-dichloroethane (5 ml) at 0°-2° C. and resulting mixture was stirred at the same temperature for 1 hr. After adding ethanol (1.06 g, 23.0 mmoles), the reaction mixture was stirred at 0°-2° C. for 20 min and heated under reflux for 2 hr. 5% Hydrochloric acid (10 ml) was added dropwise to the reaction solution and the organic layer was separated, washed successively with water and 5% aqueous solution of sodium bicarbonate, dried over sodium sulfate and concentrated under reduced pressure. Purification of the residue by silica gel column chromatography gave the desired ethyl 4-(2,4'-difluoro-4-biphenylyl)-3-oxopentanoate (1.02 g, 3.07 mmoles yield 67%) as a light yellow oil.

1H-NMR (CDC13) δ ppm : 1.25 (3H, t), 1.46 (3H, d), 3.43 (2H, q), 4.96 (1H, q), 4.12–4.21 (2H, m), 7.01–7.53 (7H, m).

REFERENCE EXAMPLE 11

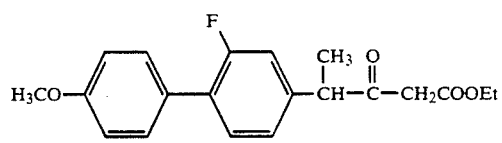

Ethyl 4-(2-fluoro-4'-methoxy-4-biphenylyl)-3-oxopentanoate was obtained from 2-(2-fluoro-4'-methoxy-4-biphenylyl)propionic acid in the same manner as in Reference Example 10.

1H-NMR (CDC13) δ ppm : 1.24 (3H, t), 1.52 (2H, d), 3.73 (1H, q), 3.85 (3H, s), 4.09–4.22 (2H, m), 6.96–7.50 (7H, m).

REFERENCE EXAMPLE 12

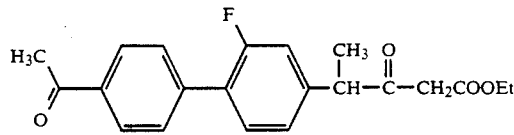

Ethyl 4-(4'-acetyl-2-fluoro-4-biphenylyl)-3-oxopentanoate was obtained from 2-(4,-acetyl-2-fluoro-4-biphenylyl)propionic acid in the same manner as in Reference Example 10.

1H-NMR (CDC13) δ ppm : 1.25 (3H, t), 1.47 (3H, d), 2.64 (3H, s), 3.35–3.65 (2H, m), 3.99 (1H, q), 4.76 (2H, q), 7.05–8.07 (7H, m).

REFERENCE EXAMPLE 13

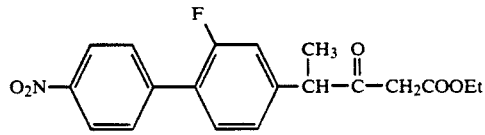

Ethyl 4-(2-fluoro-4'-nitro-4-biphenylyl)-3-oxopentanoate was obtained from 2-(2-fluoro-4'-biphenylyl)-propionic acid in the same manner as in Reference Example 10.

1H-NMR (CDCl3) δ ppm : 1.25 (3H, t), 1.48 (3H, d), 3.45 (2H, m), 4.02 (1H, q), 4.17 (2H, m), 7 09–7.18 (2H, m), 7.46 (1H, t), 7.70–7.73 (2H, m), 8.27–8.33 (2H, m).

REFERENCE EXAMPLE 14

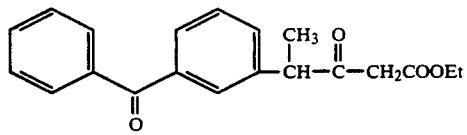

Ethyl 4-(3-benzoylphenyl)-3-oxopentanoate was obtained from 2-(3-benzoylphenyl)propionic acid in the same manner as in Reference Example 10.

1H-NMR (CDCl3) δ ppm : 1.23 (3H, t), 1.47 (3H, d), 3.40 (2H, m), 4.01 (1H, q), 4.09–4.20 (2H, m), 7.45–7.82 (9H, m).

REFERENCE EXAMPLE 15

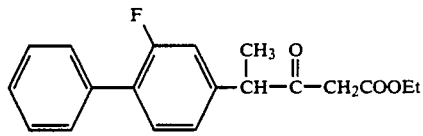

Ethyl 4-(2-fluoro-4-biphenylyl)-3-oxopentanoate was obtained from 2-(2-fluoro-4-benzoylphenyl)propionic acid (Flurbiprofen) in the same manner as in Reference Example 10.

1H-NMR (CDCl3) δ ppm : 1.25 (3H, t), 1.47 (3H, d), 3.43 (2H, m), 3.97 (q, 1H), 4.15 (q, 2H), 7.06–7.55 (m, 8H).

REFERENCE EXAMPLE 16

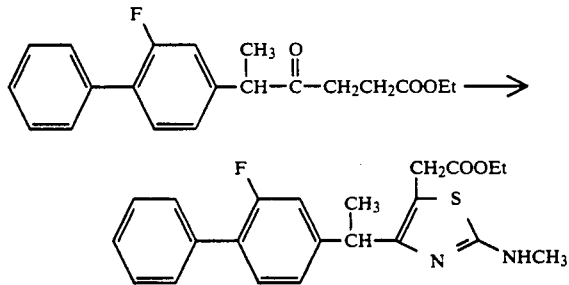

To an ice-cooled solution of 5-(2-fluoro-4-biphenylyl)-4-oxohexanoic acid (500 mg, 1.52 mmoles) in diethyl ether (10 ml) was added dropwise bromine (243 mg, 1.52 mmoles) and the resulting mixture was stirred at room temperature for 3.5 hours. The reaction mixture was concentrated under reduced pressure. A mixture of the afforded residue, N-methylthiourea (164 mg, 1.82 mmoles) and methanol was stirred at 50° C. for 2 hours and concentrated under reduced pressure. The residue was partitioned between ethyl acetate and aqueous sodium bicarbonate. The organic layer was washed with water, dried over sodium sulfate and concentrated under reduce pressure. Purification of the residue by medium pressure silica gel column chromatography gave the desired ethyl 2-(4-(1-(2-fluoro-4-biphenylyl)ethyl)-2-methylamino-5-thiazolyl)acetate (209 mg, 0.524 mmole, yield 35%) as a yellow oil.

1H-NMR (CDCl3) δ ppm : 1.23 (3H, t), 1.62 (3H, d), 2.91 (3H, d), 3.57–3.71 (3H, m), 5.08 (1H, br), 7.12–7.53 (8H, m).

REFERENCE EXAMPLE 17

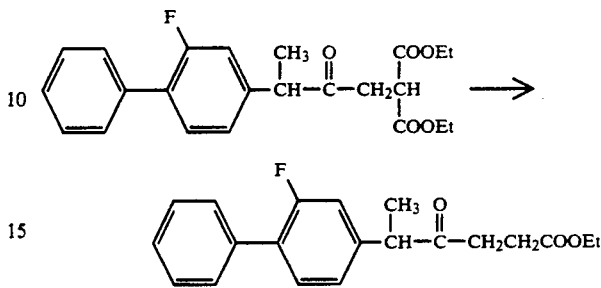

A mixture of diethyl 2-(3-(2-fluoro-4-biphenylyl)-2-oxobutyl)malonate (5.00 g, 12.5 mmoles), acetic acid (100 ml), and 30% sulfuric acid (100 ml) was heated under reflux for 4 hours. After cooling the reaction mixture was extracted with ether. The organic layer was washed with water, dried over sodium sulfate and concentrated under reduced pressure The mixture of the residue, ethanol (100 ml) and concentrated sulfuric acid (1.0 g) was heated at 50° C. for 3 hours. The reaction mixture was concentrated under reduced pressure and the residue was extracted with ether. The organic layer was washed successively with water, aqueous sodium bicarbonate and water, dried over sodium sulfate and concentrated under reduced pressure. Purification of the residue by medium pressure silica gel column chromatography gave the desired 5-(2-fluoro-4-biphenylyl)-4-oxohexanoic acid (2.21 g, 6.71 mmoles, yield 54%) as a light yellow oil.

1H-NMR (CDCl3) δ ppm : 1.23 (3H, t), 1.45 (3H, d), 2.45–2.77 (4H, m), 3.84 (1H, q), 4.10 (2H, q), 7.02–7.56 (8H, m).

REFERENCE EXAMPLE 18

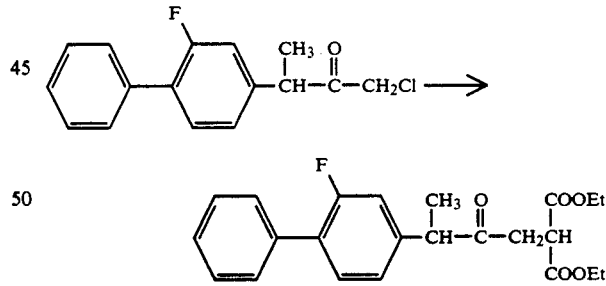

To a suspension of sodium hydride (1.88 g as 60% in oil, 47.0 mmoles) which was washed with hexane to remove mineral oil and dried, in dimethylformamide (DMF, 23 ml) was added dropwise a solution of diethyl malonate (7.52 g, 47.0 mmoles) in DMF (5 ml) at 0° C. under the stream of nitrogen gas. After elevating the temperature to 50° C., a solution of 1-chloro-3-(2-fluoro-4-biphenylyl)butan-2-one (10.0 g, 36.1 mmoles) in DMF (40 ml) was added dropwise, and the resulting mixture was stirred at the same temperature for 2 hours. The reaction mixture was poured into ice water and extracted with diethyl ether. The organic layer was washed with 1M hydrochloric acid, dried over sodium sulfate and concentrated under reduced pressure. Purification of the residue by medium pressure silica gel column chromatography gave the desired diethyl 2-(3-(2-fluoro-4-biphenylyl)-2-oxobutyl)malonate (8.98 g, 22.4 mmoles, yield 62%) as a light yellow oil.

1H-NMR (CDCl3) δ ppm : 1.20–1.31 (6H, m), 1.45 (3H, d), 2.93–3.13 (2H, m), 3.82–3.87 (2H, m), 4.11–4.25 (4H, m), 7.01–7.56 (8H, m).

REFERENCE EXAMPLE 19

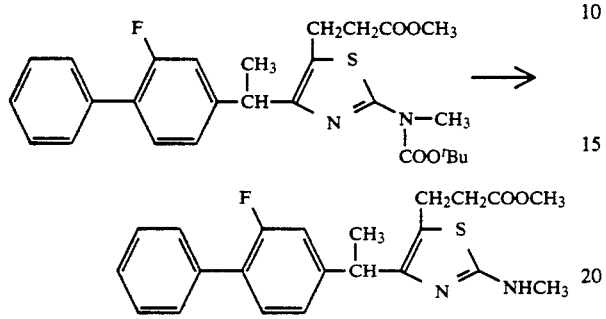

A mixture of methyl 3-(4-(1-(2-fluoro-4-biphenylyl)ethyl)-2-(N-t-butoxycarbonyl, N-methyl)amino-5-thiazolyl)propionate (1.00 g, 2.01 mmoles) and concentrated hydrochloric acid/acetic acid mixture (1:11, 20 ml) was stirred at room temperature for 4 hours. The reaction mixture was adjusted to pH 10 with 1M aqueous solution of sodium hydroxide and extracted with chloroform. The organic layer was washed with water, dried over sodium sulfate and concentrated under reduce pressure. Purification of the residue by silica gel column chromatography gave the desired methyl 3-(4-(1-(2-fluoro-4-biphenylyl)ethyl)-2-methylamino-5-thiazolyl-)-propionate (478 mg, 1.20 mmoles, yield 60%).

1H-NMR (CDCl3) δ ppm : 1.62 (3H, d), 2.52 (2H, t), 2.89 (3H, d), 2.90–3.11 (2H, m), 3.66 (3H, s), 4.12 (1H, q), 5.06 (1H, br), 7.13–7.53 (8H, m).

REFERENCE EXAMPLE 20

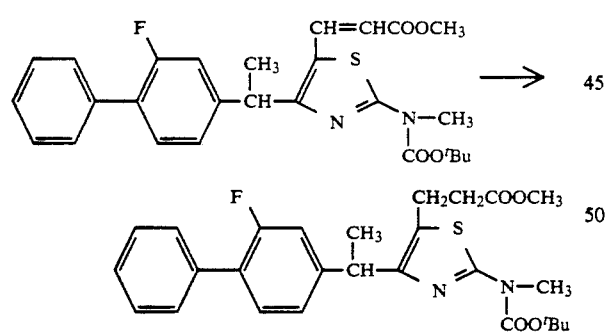

To a solution of methyl 3-(4-(1-(2-fluoro-4-biphenylyl)ethyl)-2-(N-t-butoxycarbonyl, N-methyl)amino-5-thiazolyl)acrylate (1.80 g, 3.62 mmoles) in ethanol (200 ml), was added 10% palladium carbon (2.7 g) and the resulting mixture was hydrogenated at room temperature. When consumption of hydrogen had ceased, the reaction mixture was filtered to remove the catalyst, and the filtrate was concentrated under reduced pressure. Purification of the residue by medium pressure silica gel column chromatography gave the desired methyl 3-(4-(1-(2-fluoro-4-biphenylyl)ethyl)-2-(N-t-butoxycarbonyl, N-methyl)amino-5-thiazolyl)propionate (1.10 g, 2.21 mmoles, yield 60%). Apart from it, 500 mg (1.00 mmole, 28%) of the starting compound was recovered.

1H-NMR (CDCl3) δ ppm : 1.56 (9H, s), 1.64 (3H, d), 2.55 (2H, t), 2.93–3.11 (2H, m), 3.53 (3H, s), 3.66 (3H, s), 4.16 (1H, q), 7.15–7.54 (8H, m).

REFERENCE EXAMPLE 21

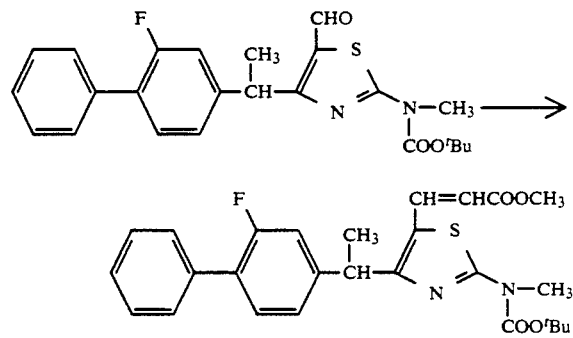

To an ice-cooled suspension of 60% sodium hydride (904 mg, 22.6 mmoles) in dimethyl sulfoxide (25 ml), was added dropwise methyl diethylphosphonoacetate (4.75 g, 22.6 mmoles) and the resulting mixture was stirred at room temperature for 30 minutes. Then, a solution of 5-formyl-4-(1-(2-fluoro-4-biphenylyl)ethyl)-2-(N-t-butoxycarbonyl, N-methyl)aminothiazole (5.0 g, 11.3 mmoles) in dimethylformamide (5.0 ml) was added dropwise, and the resulting mixture was heated with stirring at 80° C. for 10 hours. The reaction mixture was diluted with water and extracted with ethyl acetate. The organic layer was washed with water, dried over sodium sulfate and concentrated under reduced pressure. Purification of the residue by silica gel column chromatography gave the desired methyl 3-(4-(1-(2-fluoro-4-biphenylyl)ethyl)-2-(N-t-butoxycarbonyl, N-methyl)amino-5-thiazolyl)acrylate (E, Z mixture; 1.90 g, 3.83 mmoles, yield 34%).

1H-NMR (CDCl3) δ ppm : 1.58 (9H, s), 1.65 (3H, d), 3.11 & 3.55 (total 3H, each s), 3.77 (3H, d), 4.32 & 4.42 (total 1H, each s), 5.70 & 6.05 (total 1H, each d), 7.17–7.53 (8H, m), 7.89 & 8.10 (total 1H, each s).

REFERENCE EXAMPLE 22

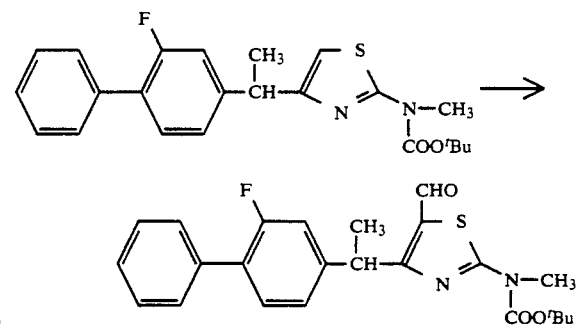

To an ice-cooled solution of dimethylformamide (188.5 g, 2.58 mmoles) in 1,2-dichlorethane (EDC, 623 ml), was slowly added dropwise a solution of phosphorus oxychloride (59.4 g) in EDC (226 ml) and the resulting mixture was stirred at room temperature for 15 minutes. After again being cooled with ice, a solution of 4-(1-(2-fluoro-4-biphenylyl)ethyl)-2-(N-t-butoxycarbonyl, N-methyl)aminothiazole (107 g, 259 mmoles) in EDC (1,132 ml) was added dropwise to the reaction mixture over a period of 40 minutes, and the resulting mixture was stirred at room temperature for one hour, heated under reflux for 3 hours, and concentrated under reduced pressure. To the afforded residue was slowly added a solution of sodium hydroxide (193 g) in water (1,930 ml) while being cooled with ice, and the resulting mixture was extracted with chloroform. The organic layer was washed with water, dried over sodium sulfate and concentrated under reduced pressure. Purification of the residue by medium pressure silica gel column chromatography gave the desired 5-formyl-4-(1-(2-fluoro-4-biphenylyl)ethyl)-2-(N-t-butoxycarbonyl, N-methyl)-aminothiazole (31.7 g, 72.0 mmoles, yield 28%).

1H-NMR (CDC13) δ ppm : 1.58 (9H, s), 1.78 (3H, d), 3.61 (3H, s), 4.73 (1H, q), 7.06-7.55 (8H, m), 10.12 (1H, s).

REFERENCE EXAMPLE 23

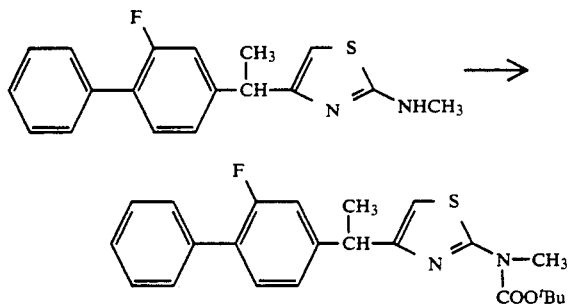

To an ice-cooled solution of 4-(1-(2-fluoro-4-biphenylyl)ethyl)-2-methylaminothiazole (100 g, 320 mmoles) and di-t-butyl dicarbonate (175 g, 802 mmoles) in tetrahydrofuran (THF, 750 ml) was added dropwise a solution of 1,8-diazabicyclo[5.4.0]-7-undecene (DBU, 60 g, 394 mmoles) in THF (90 ml) and the resulting mixture was heated at 50° C. for 13 hours. The reaction mixture was concentrated under reduced pressure, and the residue was diluted with chloroform and washed successively with water, 1M hydrochloric acid (3 times) and water. The organic layer was dried over sodium sulfate and concentrated under reduced pressure and the residue was purified by medium pressure silica gel column chromatography. The crystalline product thus obtained was washed with methanol to obtain the desired 4-(1-(2-fluoro-4-biphenylyl)ethyl)-2-(N-t-butoxycarbonyl, N-methyl)aminothiazole (109 g, 263 mmoles, yield 82%) as a white colored crystalline product.

m.p. 98°-98.5° C.

What is claimed is:

1. A thiazole compound represented by the formula:

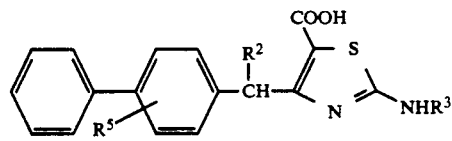

wherein each of $R^2$ and $R^3$ independently represents a $C_{1-4}$ alkyl group and $R^5$ is a halogen atom, or a pharmaceutically acceptable salt thereof.

2. A thiazole compound according to claim 1, wherein $R^2$ is a methyl group, or a pharmaceutically acceptable salt thereof.

3. A thiazole compound according to claim 1, wherein $R^3$ is a methyl group, or a pharmaceutically acceptable salt thereof.

4. A thiazole compound according to claim 1, wherein $R^5$ is a fluorine atom, or a pharmaceutically acceptable salt thereof.

5. A thiazole compound according to claim 1, wherein each of $R^2$ and $R^3$ is a methyl group and $R^5$ is a fluorine atom, or a pharmaceutically acceptable salt thereof.

6. A thiazole compound represented by the formula:

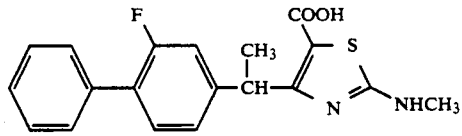

or a pharmaceutically acceptable salt thereof.

7. A pharmaceutical composition for treatment of rheumatoid arthritis or systemic lupus erthyematosus, which comprises an active ingredient of a pharmaceutically effective amount of at least one compound as claimed in claim 1 or a pharmaceutically acceptable salt thereof, and at least one pharmaceutically acceptable inert carrier or diluent.

8. A method for treatment of rheumatoid arthritis or systemic lupus erthyematosus, which comprises administering to a person a pharmaceutically effective amount of at least one compound as claimed in claim 1 or a pharmaceutically acceptable salt thereof.

* * * * *